United States Patent
Abel Fernandez

(10) Patent No.: US 12,165,770 B2
(45) Date of Patent: *Dec. 10, 2024

(54) SYSTEM AND METHOD FOR DETECTING NEUROLOGICAL DISORDERS AND FOR MEASURING GENERAL COGNITIVE PERFORMANCE

(71) Applicant: Viewmind, Inc., New York, NY (US)

(72) Inventor: Gerardo Abel Fernandez, Bahia Blanca (AR)

(73) Assignee: Viewmind, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/217,688

(22) Filed: Jul. 3, 2023

(65) Prior Publication Data

US 2023/0352175 A1 Nov. 2, 2023

Related U.S. Application Data

(63) Continuation of application No. 16/768,738, filed as application No. PCT/IL2018/051316 on Nov. 30, 2018, now Pat. No. 11,694,803.

(Continued)

(51) Int. Cl.
| | |
|---|---|
| *G16H 50/20* | (2018.01) |
| *A61B 3/00* | (2006.01) |
| *A61B 3/11* | (2006.01) |
| *A61B 3/113* | (2006.01) |
| *A61B 5/00* | (2006.01) |

(Continued)

(52) U.S. Cl.
CPC ........... *G16H 50/20* (2018.01); *A61B 3/0025* (2013.01); *A61B 3/0041* (2013.01); *A61B 3/112* (2013.01); *A61B 3/113* (2013.01); *A61B 5/162* (2013.01); *A61B 5/163* (2017.08); *A61B 5/168* (2013.01); *A61B 5/4058* (2013.01); *A61B 5/4082* (2013.01); *A61B 5/4088* (2013.01); *A61B 5/7267* (2013.01); *G06N 20/00* (2019.01); *G16H 40/63* (2018.01)

(58) Field of Classification Search
CPC ...... G16H 50/20; G16H 40/63; A61B 3/0025; A61B 3/0041; A61B 3/112; A61B 3/113; A61B 5/162; A61B 5/163; A61B 5/168; A61B 5/4058; A61B 5/4082; A61B 5/4088; A61B 5/7267; G06N 20/00
USPC ....................................................... 600/558
See application file for complete search history.

(56) References Cited

U.S. PATENT DOCUMENTS

| | | |
|---|---|---|
| 10,602,927 B2 | 3/2020 | Krueger |
| 11,393,564 B2 * | 7/2022 | Gross ............... G16H 50/30 |

(Continued)

FOREIGN PATENT DOCUMENTS

| | | |
|---|---|---|
| WO | 2013/148557 A1 | 10/2013 |
| WO | 2021/021328 A2 | 2/2021 |
| WO | 2022/140498 A1 | 6/2022 |

OTHER PUBLICATIONS

Biondi, J., et al., "Eye-Movement behavior identification for AD diagnosis", arXiv:1702.00837, Feb. 2, 2017, pp. 1-11.

*Primary Examiner* — Mohammed A Hasan
(74) *Attorney, Agent, or Firm* — Stuart H. Mayer; Kaplan Breyer Schwarz LLP

(57) ABSTRACT

Methods and systems useful for detecting neurological disorders and for measuring general cognitive performance, in particular by measuring eye movements and/or pupil diameter during eye-movement tasks.

5 Claims, 10 Drawing Sheets

Related U.S. Application Data

(60) Provisional application No. 62/617,622, filed on Jan. 16, 2018, provisional application No. 62/592,517, filed on Nov. 30, 2017.

(51) Int. Cl.
*A61B 5/16* (2006.01)
*G06N 20/00* (2019.01)
*G16H 40/63* (2018.01)

(56) References Cited

U.S. PATENT DOCUMENTS

| | | | |
|---|---|---|---|
| 11,694,803 B2 * | 7/2023 | Abel Fernandez | A61B 5/163 600/558 |
| 2005/0175218 A1 * | 8/2005 | Vertegaal | G06T 7/254 345/157 |
| 2009/0306741 A1 | 12/2009 | Hogle et al. | |
| 2012/0264719 A1 | 10/2012 | Boulton et al. | |
| 2015/0245766 A1 | 9/2015 | Rennaker et al. | |
| 2016/0022136 A1 | 1/2016 | Ettenhofer et al. | |
| 2016/0022137 A1 * | 1/2016 | Wetzel | A61B 5/4082 600/558 |
| 2017/0112427 A1 | 4/2017 | Simon et al. | |
| 2017/0135577 A1 | 5/2017 | Komogortsev | |
| 2017/0293356 A1 | 10/2017 | Khaderi et al. | |
| 2018/0235549 A1 | 8/2018 | Sereno et al. | |
| 2019/0307384 A1 | 10/2019 | Baeuerle | |
| 2020/0242957 A1 | 7/2020 | Delis et al. | |
| 2021/0093240 A1 | 4/2021 | Douglas et al. | |
| 2021/0174959 A1 | 6/2021 | Abel Fernandez | |

* cited by examiner

SYSTEM AND METHOD FOR DETECTING NEUROLOGICAL DISORDERS AND FOR MEASURING GENERAL COGNITIVE PERFORMANCE

CROSS REFERENCE TO RELATED APPLICATION

This application is a continuation of U.S. Ser. No. 16/768,738, filed Jun. 1, 2020, which is a 371 of International Application No. PCT/IL2018/051316, filed Nov. 30, 2018 and claims the benefit of U.S. Provisional Application No. 62/592,517, filed Nov. 30, 2017 and U.S. Provisional Application Ser. No. 62/617,622, filed Jan. 16, 2018, the contents of which are incorporated herein by reference in their entireties.

FIELD OF THE INVENTION

The invention relates to systems and methods for detecting neurological disorders and for measuring general cognitive performance, in particular by measuring eye movements and/or pupil diameter during eye-movement tasks.

BACKGROUND TO THE INVENTION

Using eye tracking as a diagnostic tool has been implemented in the art:

U.S. Pat. No. 4,889,422 discloses an automated system for determining the existence of dyslexia. The system comprises an eye stimulus means, an eye movement detector, a processor that collects data representing eye positions over time, and an analysis program for analyzing the data and categorizing the eye movements into micromovements, saccade movements, pursuit movements, convergent divergent movements, fixations and blinks. If the total number of fixations is greater than the number of visual stimuli, then a first indicator that dyslexia is present is registered.

Fielding et al published "Ocular motor measures of cognitive dysfunction in multiple sclerosis II: working memory" (J Nerol, published online 9 Apr. 2015), which discloses an experiment in which working memory of patients with clinically-definite multiple sclerosis (CDMS) or clinically isolated syndrome (CIS) were tested for working memory by an ocular test which measured task errors, saccade latency, and relative sensitivity to loading of working memory There is a long felt need for a widely availability tool for diagnosing neurological disorders.

SUMMARY OF THE INVENTION

It is the object of the present invention to provide a system for detecting one or more neurological disorders in a subject by measuring eye movements; the measuring of eye movements performed while the subject is reading; the system comprising
  a. an eye tracker [10], configured to monitor eye movements of a subject [5] while the subject [5] is reading a text [15];
  b. a processor [20], configured to receive data from the eye tracker while the subject [5] is reading the text [15]; and
  c. a display means configured to display a test report received from the processor [20];
wherein the processor is further configured to analyze the eye-tracking data for evidence of one or more neurological disorders or general cognitive performance and to report, in the test report [50], a detection of one or more neurological disorders or a measure of cognitive performance of the subject [5].

It is another object of the present invention as described above, wherein the processor is further configured, upon receiving the eye-tracking data from the eye tracker, to:
  a. count a total number of ocular fixations of a subject while reading the text; and
  b. if the total number of ocular fixations of a subject when reading is higher than for a control group, then report in the test report that a compromise in attentional processes is detected.

It is another object of the present invention as described above, wherein the processor is further configured, upon receiving the eye-tracking data from the eye tracker, to:
  a. count a number of forward ocular fixations of the subject while reading the text; and
  b. if the number of forward ocular fixations of the subject is lower than for the control group; and the number of ocular fixations of a subject when reading is higher than for the control group, then report in the test report that a compromise in working memory is detected.

It is another object of the present invention as described above, wherein the processor is further configured, upon receiving the eye-tracking data from the eye tracker, to:
  a. count a number of words that the subject fixated on only once while reading the text; and
  b. if the number of words that the subject fixated on only once is lower than for the control group, then report in the test report that a compromise in retrieval memory is detected.

It is another object of the present invention as described above, wherein the processor is further configured, upon receiving the eye-tracking data from the eye tracker, to:
  a. count a number of multiple ocular fixations of the subject while reading the text; and
  b. if the number of multiple ocular fixations is higher than for the control group, then report in the test report that a compromise in executive processes is detected.

It is another object of the present invention to detecting one or more neurological disorders in a subject by measuring eye movements, wherein the processor is further configured, upon receiving the eye-tracking data from the eye tracker, to
  a. compute an average saccade amplitude from one ocular fixation to a next ocular fixation; and
  b. if the average saccade amplitude is lower than for the control group, then report in the test report that a compromise in executive processes is detected.

It is another object of the present invention as described above, further comprising a means for measuring a pupil diameter of the subject, wherein the processor is further configured to
  a. track the pupil diameter of the subject reading the text; and
  b. if the pupil diameter of the subject does not show a reduction as advancing in reading the text, then report in the test report that that a compromise in executive processes is detected.

It is the object of the present invention to provide a system for detecting one or more neurological disorders and to check cognitive performance in a subject by measuring eye movements and pupil behavior and applying an intelligent algorithm; the measuring of eye movements performed while the subject is reading; the system comprising a. an eye tracker [10], the eye tracker configured to monitor eye movements and pupil behavior of a subject [5] while the subject [5] is reading a text [15];
b. a processor [20], the processor configured to receive data from the eye tracker while the subject [5] is reading the text [15];
c. an intelligent algorithm for learning, identifying, typifying and classifying eye movements features in pathologies and within pathologies; and
d. a display means [40], the display configured to display the output of the intelligent algorithm on a test report received from the processor [20];

wherein the processor is further configured to analyze and modeling the eye-tracking data for evidence of one or more neurological disorders and from cognitive performance and to report, in the test report [50], a detection and classification of the one or more neurological disorders of the subject [5] both, between and within pathologies.

It is another object of the present invention as described above, wherein the processor is further configured, upon receiving the eye-tracking data from the eye tracker, to identify and classifying eye movement features and pupil behavior during reading the text providing an output of the classifier for reporting in the test report a subject's cognitive performance and/or pathological classification (i.e, the pathology that correspond to the subject because his/her eye movement features); and a value within the pathology (i.e., the level of cognitive, behavioral and biological compromise that the subject shows within a particular pathology).

It is another object of the present invention as described above, wherein the intelligent algorithm is configured to read at least one input, the input selected from a group consisting of:
a. Index of total number of ocular fixations of a subject while reading the text.
b. Index of forward ocular fixations of the subject while reading the text.
c. Index of words that the subject fixated on only once while reading the text
d. Index of multiple ocular fixations of the subject while reading the text
e. Average saccade amplitude from one ocular fixation to a next ocular fixation
f. Pupil diameter of the subject reading the text
g. Index of blinks coming from the left eye, the right eye or from both eyes.
h. Microsaccades' Factors of Form (FF):
  i. HEWI: shows the micro-saccade's height/width relationship.
  ii. AREA: shows the area of the rectangle in which the micro-saccade is inscribed.
  iii. LONG: is the longitude of the horizontal-vertical plane trajectory of the micro-saccade.
  iv. ANG: is the sum of all the angles in the plane horizontal-vertical plane of the micro-saccade.
  v. AANG: is the sum of all the absolute values of angles in radians in the plane horizontal-vertical plane of the micro-saccade. These last two FF gives an estimation of the micro-saccadic trajectory regularity.
  vi. MOD and THETA: are the modulus and the angle of the polar coordinates of the sum of the cartesian coordinates. They give a spatial orientation of the micro-saccade relative to the median of the fixation.
  vii. TIME: is the time duration in milliseconds of the micro-saccade.
  viii. VMIN and VMAX: are the minimum and maximum velocities of the microsaccades in degrees per second.
  ix. Micro-saccade rate: is the instantaneous rate in each time bin.
  x. Directional congruency: is the congruency between the micro-saccade direction and the location of the stimulus.
i. Eye position coming from the left eye, the right eye or from both eyes (i.e., abscissa and ordinate coordinate) during reading the text.
j. Fixation sequence (i.e., ocular behavior) during reading the text. The sequence will be available from images, from matrices, etc.
k. Distance of separation between ocular fixations during reading the text.
l. Filia information of the subject (i.e., age; years of education; sex; ethnic group; occupation; hours per week of physical activity).
m. Total reading time (i.e., the time that the subject spent when reading the text).

It is the object of the present invention to provide a method for evaluating compromises in neurological functions associated with Multiple Sclerosis [MS], the method comprising
a. providing a system for evaluating compromises in neurological functions associated with MS [305];
b. requesting a subject to fixate on a reference target of a chart [310];
c. for a number of repetitions, presenting a stimulus image in one of the zones to the subject [315]; the subject is requested to remember which zone each stimulus image appeared and in what order;
d. presenting to the subject a cue corresponding to one of the presented stimulus images [320];
e. measuring a saccade of the subject in response to the step of presenting a cue; the subject is requested to look at the zone in which the stimulus image was the presented corresponding to the cue;
f. repeating steps of presenting a cue and measuring a saccade [330];
g. repeating steps b-f for a number of trials [335];
h. calculating one or more of:
  i. a WM effect (i.e. WM effect is a measure that increases when WM demand increases. For each cue number, the WM effect is represented by the ratio between the number of errors reported by the subject through all the trials, and the number of trials); and
  ii. an average saccadic latency [345], saccadic latency defined as an amount of time for the subject to initiate a saccade to the zone; and
i. reporting one or more of:
  i. a degree of compromise in working memory [350], with increased WM effect; and
  ii. a degree of compromise in executive processes [355], with increased saccadic latency;
j. wherein the method further comprises additional steps comprising measurements performed during the step of presenting a stimulus image [315], during which the subject is further requested to look at the stimulus image; the measurements comprising measuring one or more of
  i. an amplitude of pupillary dilatation of the subject [360];
  ii. a number of fixations made by the subject on the stimulus image [365]; and iii. a gaze duration by the subject on the stimulus image [370]; and
k. the additional steps further comprising calculating and reporting one or more of
i. a degree of compromise of subcortical processes [375], with increased the amplitude of pupillary dilatation;
ii. a degree of compromise of executive processes [380], with increased the number of fixations; and
iii. a degree of compromise of executive processes and working memory [385], with increased the gaze duration.

It is another object of the present invention as described above, wherein the reference target is at a central position of the chart and the plurality of zones are disposed around the reference target.

It is another object of the present invention as described above, wherein the cue is disposed at a position of the reference target.

It is another object of the present invention as described above, wherein the errors defined as eye movement towards a location other than the correct zone and/or no saccade initiated within a time limit.

It is another object of the present invention as described above, wherein a cue corresponding to a first presented stimulus is excluded from the presented cue numbers.

It is another object of the present invention as described above, wherein a saccade is included in the step of calculating the WM effect and the saccadic latency only if the saccade is initiated more than a minimum saccade latency after the step of presenting the cue number.

It is another object of the present invention as described above, wherein the saccade is excluded from calculating WM if: no saccade to one of the zones is made within a time limit, failing to maintain the fixation on the reference target before onset of a saccade to one of the angular zones, and blinking causing eye motion to be indeterminate It is the object of the present invention to provide a system for detecting one or more neurological disorders in a subject by measuring eye movements; the measuring of eye movements performed while the subject is carrying out the visual test; the system comprising
a. an eye tracker [10], configured to monitor eye movements of a subject [5] while the subject [5] is carrying out the visual test [15];
b. requesting a subject to fixate sequentially on targets that are part of a group of targets (e.g., point) presented together in the same picture (i.e., labyrinth or maze) [605];
c. requesting a subject to fixate only one target each time until finishing visualizing all the targets through the picture following the labyrinth or maze direction (i.e., entering from the bottom and exiting through the top of said labyrinth or maze) [610].
d. a processor [20], configured to receive data from the eye tracker while the subject [5] is carrying out the visual test [15]; and
e. a display means configured to display a test report received from the processor [20];
wherein the processor is further configured to analyze the eye-tracking data for evidence of neurological and attentional disorders and to report, in the test report [50], a detection of the one or more neurological and attentional disorder of the subject [5].

It is another object of the present invention as described above, wherein the processor is further configured, upon receiving the eye-tracking data from the eye tracker while the subject is visualizing, recognizing, maintaining, controlling, inhibiting and sequencing targets, to:
a. count a total number of ocular fixations of a subject while performing the visual test; and
b. if the total number of ocular fixations of a subject when visualizing targets is higher than for a control group, then report in the test report that a compromise in attentional processes is detected.

It is another object of the present invention as described above, wherein the processor is further configured, upon receiving the eye-tracking data from the eye tracker, to:
a. measure the saccade average speed while the subject is shifting from one target to the other; and
b. if the saccade average speed of the subject is lower than for the control group; then report in the test report that a compromise in executive functions is detected.

It is another object of the present invention as described above, wherein the processor is further configured, upon receiving the eye-tracking data from the eye tracker, to:
a. count a number of correct target recognitions [625]; and
b. if the number of correct target recognitions that the subject is lower than for the control group, then report in the test report that a compromise in working memory is detected.

It is another object of the present invention as described above, wherein the processor is further configured, upon receiving the eye-tracking data from the eye tracker, to:
a. compute an average saccade amplitude [630]; and
b. if the average saccade amplitude is lower than for the control group, then report in the test report that a compromise in executive processes is detected.

It is another object of the present invention as described above, wherein the processor is further configured, upon receiving the eye-tracking data from the eye tracker, to:
a. the total time spent to perform the visual test [635]; and
b. if the total time spent to perform the visual test is higher than for the control group, then report in the test report that a compromise in attentional processes is detected.

It is another object of the present invention as described above, further comprising a means for measuring a pupil diameter of the subject, wherein the processor is further configured to:
a. track the pupil diameter of the subject performing the visual test; and
b. if the pupil diameter of the subject does not show an increase when advancing in performing the task, then report in the test report that that a compromise in attentional processes is detected.

It is another object of the present invention as described above, further comprising a means for measuring a pupil diameter of the subject, wherein the processor is further configured for calculating fixation durations on targets of person while performing the visual test, if the fixation duration of the subject while fixating on targets is lower than for the control group, then report in the test report that that a compromise in attentional and executive processes is detected.

It is the object of the present invention to provide a method for detecting the presence of one or more neurological disorders or for measuring general cognitive performance in a subject by measuring eye movements of the subject; the measuring of eye movements performed while the subject is reading [405]; the method comprising steps of:
a. providing the system for detecting one or more neurological disorders;
b. receiving eye-tracking data and/or pupil diameter data of a subject while the subject is reading a text [415];

wherein the method further comprises steps of analyzing the eye-tracking data and/or pupil diameter data for evidence of one or more neurological disorders and displaying a report of a detection of the neurological disorder(s) [499].

It is another object of the present invention as described above, further comprising steps of:
- a. counting a total number of ocular fixations of the subject while the subject is reading the text [420]; and
- b. if the total number of ocular fixations of the subject while reading the text is higher than for a control group, then reporting that a compromise in attentional processes is detected [460].

It is another object of the present invention as described above, further comprising steps of
- a. counting a total number of ocular fixations of the subject while the subject is reading the text [420];
- b. counting a number of forward ocular fixations of the subject while the subject is reading the text [430]; and
- c. if the number of forward ocular fixations of the subject while reading the text [430] is lower than for the control group; and the number of ocular fixations of a subject when reading is higher than for the control group, then reporting that a compromise in working memory is detected [470].

It is another object of the present invention as described above, further comprising steps of:
- a. counting numbers of ocular fixations by the subject on each word in the text while the subject is reading the text [440];
- b. counting a number of the words that the subject fixated on only once while reading the text [445]; and
- c. if the number of words that the subject fixated on only once while reading the text is lower than for the control group, then reporting that a compromise in retrieval memory is detected [480].

It is another object of the present invention as described above, further comprising steps of:
- a. counting a number of multiple ocular fixations of the subject while reading the text [450]; and
- b. if the number of multiple ocular fixations of the subject while the subject is reading the text is higher than for the control group, then reporting that a compromise in executive processes is detected [490].

It is another object of the present invention as described above, further comprising steps of:
- a. computing an average saccade amplitude of the subject from one ocular fixation to a next ocular fixation while reading the text [454]; and
- b. if the average saccade amplitude of the subject from one ocular fixation to a next ocular fixation while reading the text is lower than for the control group, then reporting in the test report that a compromise in executive processes is detected [491].

It is another object of the present invention as described above, further comprising steps of:
- a. tracking a pupil diameter of the subject reading the text [456];
- b. if the pupil diameter of the subject reading the text does not show a reduction as advancing in reading the text, then reporting in the test report that a compromise in executive processes is detected [492].

It is the object of the present invention to present a system for detecting a disorder of memory binding function of a subject, the system comprising:
- a. an eye tracker [10];
- b. a means for measuring pupil diameters;
- c. a processor [20], configured to:
  - i. receive eye-tracking data of a subject [5] from the eye tracker [10];
  - ii. receive pupil diameter data of the subject [5] from the means for measuring pupil diameters; and
- d. a display means configured to display a test report received from the processor [20];

wherein the processor is further configured to analyze the eye-tracking and pupil diameter data and to report, in the test report [50], a detection of one or more disorders of memory binding function of the subject [5].

It is another object of the present invention as described above, wherein the processor is further configured, upon receiving the eye-tracking data from the eye tracker [10], to:
- a. measure one or more gaze durations of the subject [5] on each of one or more targets viewed by the subject [5];
- b. calculate an average gaze duration of the targets by the subject [5]; and
- c. report in the test report that a compromise in encoding and recognition of targets is detected in the subject [5], if the average gaze duration of the subject [5] is longer than the average gaze duration of a control group.

It is another object of the present invention as described above, wherein the processor is further configured, upon receiving the eye-tracking data from the eye tracker [10], to:
- a. count a number of ocular fixations performed by the subject [5] while viewing one or more targets; and
- b. report in the test report that a compromise in attentional processes is detected in the subject [5], if the number of ocular fixations performed by the subject [5] while viewing the targets is higher than for a control group.

It is another object of the present invention as described above, wherein the processor is further configured to applying an intelligent algorithm and to:
- a. receive a pupil diameter of the subject [5] from the means for measuring pupil diameter, while the subject [5] performs activities requiring lower cognitive effort;
- b. receive a pupil diameter of the subject [5] from the means for measuring pupil diameter, while the subject [5] performs activities requiring a stronger cognitive effort; and
- c. report in the test report that a compromise in cognitive resources is detected in the subject [5], if the pupil diameter of the subject [5], while performing the activities requiring the stronger cognitive effort, does not show an increase over the pupil diameter of the subject [5] while performing the activities requiring reduced/minimal cognitive effort.

It is another object of the present invention as described above, wherein the processor further reports a result in the test report [50], for the disorder of memory binding function not detected by the system in the subject [5].

It is the object of the present invention to provide a method for detecting a disorder of memory binding function of a subject [505], the method comprising steps of:
- a. providing a system for detecting one or more cognitive disorders;
- b. Presenting targets [510];
- c. Requesting a subjects to fixate on targets and to remember them (Encoding) [515];
- d. Presenting an empty screen [520];
- e. Presenting targets and requesting a subject to identify if the targets are exactly the same that were viewed before (Recognition). If the targets are exactly the same an answer saying "same" must be given. If not exactly the same, an answer saying "different must be given. Both answers must be collected using a keyboard or similar support [525]. Repeating steps from [510-525] for a number of trials [530];
f. Repeating steps [510-525] for a number of trials [530];
g. receiving eye-tracking data;
h. viewing by a subject of one or more targets [540];
i. measuring the gaze duration of the subject on each of the targets [545];
j. calculating an average gaze duration of the targets by the subject [550];
k. measuring a pupil diameter of the subject while performing activities requiring lower cognitive effort [555];
l. counting a number of ocular fixations performed by the subject while viewing the targets [560];
m. wherein the method further comprises steps of:
  i. reporting that a compromise in a target encoding and recognition process is detected in the subject, if the average gaze duration of the subject is longer than an average gaze duration of a control group [565];
  ii. reporting that a compromise in cognitive resources is detected in the subject, if the pupil diameter of the subject while performing the activities requiring a stronger cognitive effort does not show an increase over the pupil diameter of the subject while performing the activities requiring lower cognitive effort [570]; and
  iii. reporting that a compromise in attentional processes is detected in the subject, if the number of ocular fixations performed by the subject while viewing the targets is higher than for a control group [575].

It is another object of the present invention as described above, wherein the intelligent algorithm is configured to read at least one input, the input selected from a group consisting of:
a. Total number of ocular fixations of a subject while performing each Binding Task.
b. Binding Evaluation Task, i.e. "Bound Colors" of "Unbound Colors".
c. Identification Number of Binding Trial.
d. The Correct Behavioral Answer of the trial (i.e., if "same" or "different").
e. Subject's Behavioral response.
f. Part of the Trial i.e., encoding or retrieval.
g. Pupil diameter of the subject while performing while performing the Binding Evaluation.
h. Number of blinks coming from the left eye, the right eye or from both eyes.
i. Microsaccades; Factors of Form (FF):
  i. HEWI: shows the microsaccade's height/width relationship.
  ii. AREA: shows the area of the rectangle in which the microsaccade is inscribed.
  iii. LONG: is the longitude of the horizontal-vertical plane trajectory of the microsaccade.
  iv. ANG: is the sum of all the angles in the plane horizontal-vertical plane of the microsaccade.
  v. AANG: is the sum of all the absolute values of angles in radians in the plane horizontal-vertical plane of the microsaccade. These last two FF give an estimation of the microsaccadic trajectory regularity.
  vi. MOD and THETA: are the modulus and the angle of the polar coordinates of the sum of the cartesian coordinates. They give an spatial orientation of the microsaccade relative to the median of the fixation.
  vii. TIME: is the time duration in milliseconds of the microsaccade.
  viii. VMIN and VMAX: are the minimum and maximum velocities of the microsaccades in degrees per second.
  ix. Microsaccade rate: is the instantaneous rate in each time bin.
  x. Directional congruency: is the congruency between the microsaccade direction and the location of the stimulus.
j. Eye position coming from the left eye, the right eye or from both eyes (i.e., abscissa and ordinate coordinate) while performing the Binding Evaluation.
k. Saccade amplitude while processing targets.
l. Fixation sequence (i.e., ocular behavior) during processing targets. The sequence will be available from images, from matrices, etc.
m. Distance between the fixation point of the Right Eye and the Left Eye while performing the Binding Evaluation.
n. Filia information of the subject (i.e., age; years of education; sex; ethnic group; occupation; hours per week of physical activity).
o. Fixation duration while processing targets.
p. Gaze duration while processing targets.
q. Number of fixations on each target.
r. Number of fixations outside each target.
s. Number of fixation on each target.

It is the object of the present invention to provide a method for detecting a neurological and attentional disorders of a subject, the method comprising steps of:
a. providing an eye tracker [10];
b. a means for measuring pupil diameters;
c. a processor [20], configured to:
  i. receive eye-tracking data of a subject [5] from the eye tracker [10];
  ii. receive pupil diameter data of the subject [5] from the means for measuring pupil diameters; and
  iii. a display means configured to display a test report received from the processor [20];
wherein the processor is further configured to analyze the eye-tracking and pupil diameter data and to report, in the test report [50], a detection of one or more neurological and attentional disorders of the subject [5].

It is another object of the present invention as described above, wherein the processor is further configured, upon receiving the eye-tracking data from the eye tracker [10], to:
a. measure one or more fixation durations of the subject [5] on each of one or more targets viewed by the subject [5];
b. calculate an average saccade amplitude from each target to the other one by the subject [5]; and
c. report in the test report that a compromise in visualizing, recognizing, maintaining, controlling, inhibiting and sequencing of targets is detected in the subject [5], if the average saccade amplitude of the subject [5] is shorter than the average saccade amplitude of a control group.

It is another object of the present invention as described above, wherein the processor is further configured, upon receiving the eye-tracking data from the eye tracker [10], to:
a. count a number of ocular fixations performed by the subject [5] while viewing one or more targets; and
b. report in the test report that a compromise in attentional processes is detected in the subject [5], if the number of ocular fixations performed by the subject [5] while viewing the targets is higher than for a control group.

It is another object of the present invention as described above, wherein the processor is further configured to:

a. receive a pupil diameter of the subject [5] from the means for measuring pupil diameter, while the subject [5] performs activities requiring major attention resources;
b. receive a pupil diameter of the subject [5] from the means for measuring pupil diameter, while the subject [5] performs activities requiring a major attention; and
c. report in the test report that a compromise in cognitive resources is detected in the subject [5], if the pupil diameter of the subject [5], while performing the activities requiring the major attention, does not show an increase over the pupil diameter of the subject [5] while performing the activities requiring minor attention.

It is the object of the present invention to provide a method for detecting a neurological and executive disorder of a subject, the method comprising steps of
a. providing a system as described above;
b. receiving eye-tracking data;
c. viewing by a subject of one or more targets [605-610];
d. calculating an average saccade amplitude of the targets by the subject [630];
e. measuring a pupil diameter of the subject while performing activities requiring major attention [640];
f. measuring a pupil diameter of the subject while performing activities requiring a major attention than the minor attention; and
g. counting a number of ocular fixations performed by the subject while viewing the targets [615];
h. wherein the method further comprises steps of:
 i. reporting that a compromise in a target visualizing, recognizing, maintaining, controlling, inhibiting and sequencing process is detected in the subject, if the average saccade amplitude of the subject is shorter than an average saccade amplitude of a control group;
 ii. reporting that a compromise in cognitive and functional resources is detected in the subject, if the pupil diameter of the subject while performing the activities requiring a major attention does not show an increase over the pupil diameter of the subject while performing the activities requiring minor attention; and
 iii. reporting that a compromise in attentional processes is detected in the subject, if the number of ocular fixations performed by the subject while viewing the targets is higher than for a control group.
 iv. reporting that a compromise in executive process is detected in the subject, if the average saccade latency (speed) of the subject is shorter than an average saccade latency of a control group;

It is another object of the present invention as described above, wherein the method is configured to report that a compromise in executive process is detected in the subject, if the average saccade duration of the subject is shorter than an average fixation duration of a control group.

It is another object of the present invention as described above, wherein the neurological disorder is selected from the group consisting of Parkinson Disease or Attention Deficit Hyperactive Disorder.

DETAILED DESCRIPTION

The term "cognitive effort" reflects the total amount of mental effort that a subject needs to perform a task. In this application, the term "lower cognitive effort" refers to a reduction on working memory demands when performing a task.

In this application, the term "Microsaccades", also known as "flicks", are small saccades performed during the fixation periods. They are the largest and fastest of the fixational eye movements. In this application, the term "saccades" relate to quick, simultaneous movement of both eyes between two or more phases of a fixation.

In this application the term "Ocular drift" is the fixational eye movement characterized by a smoother, slower, roaming motion of the eye when fixed on an object.

In this application the term "Ocular microtremors" (OMTs) are small, quick, and synchronized oscillations of the eyes occurring at frequencies in a range of 40 to 100 Hz, although they typically occur at around 90 Hz in the average healthy individual. They are characterized by their high frequency and minuscule amplitude of just a few arcseconds.

In this application the terms "stimulus image" refers to a specific visual pattern or targets presented to the subject in the display. The term "visual task" or "visual test" refers to the activity that performs the subject while processing each stimulus image.

Non-limiting embodiments of the invention are now described in detail.

Figure 1:
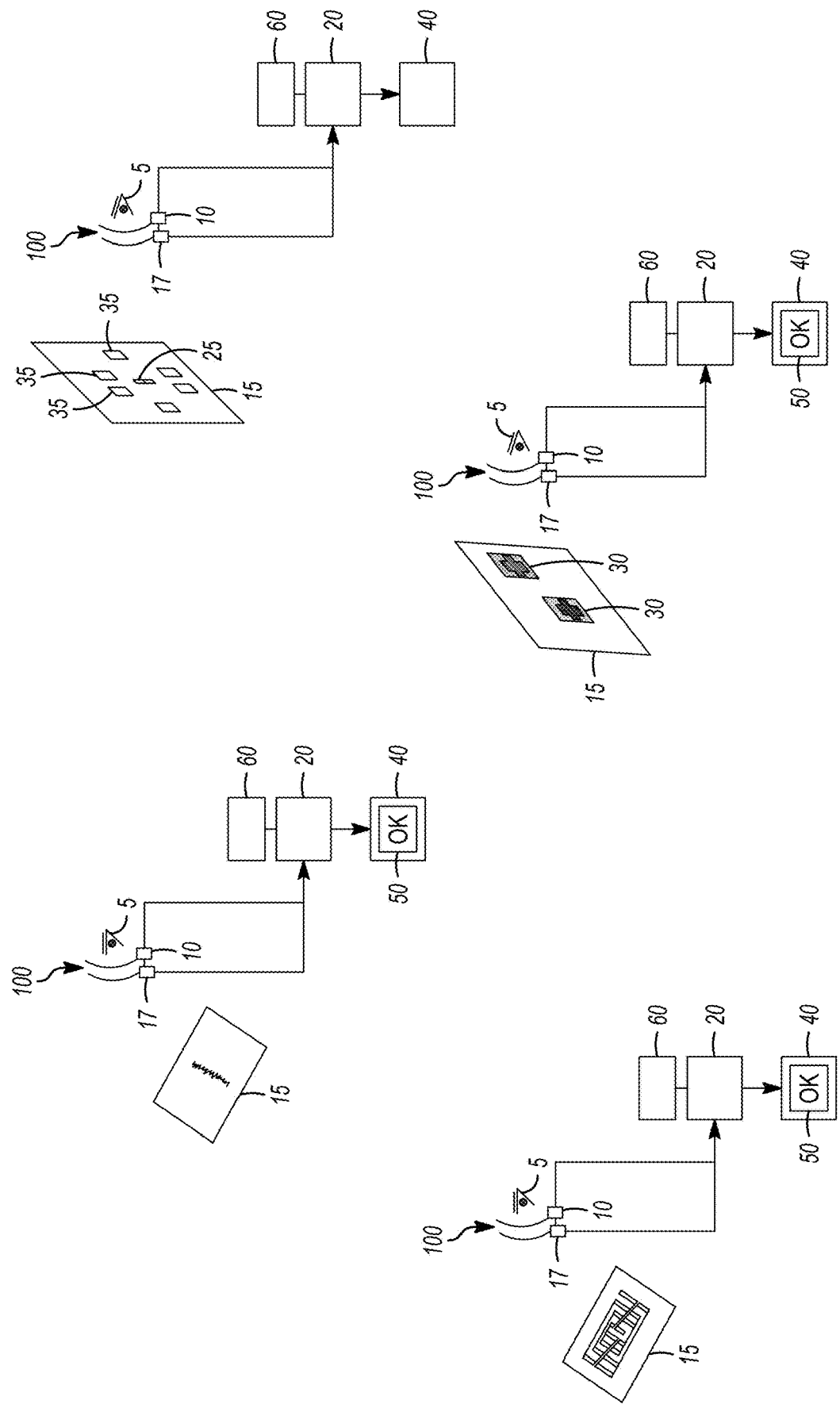
FIG. 1 shows and FIG. 2 system for detecting one or more neurological disorders of a subject, according to some embodiments of the invention.
Figure 2:
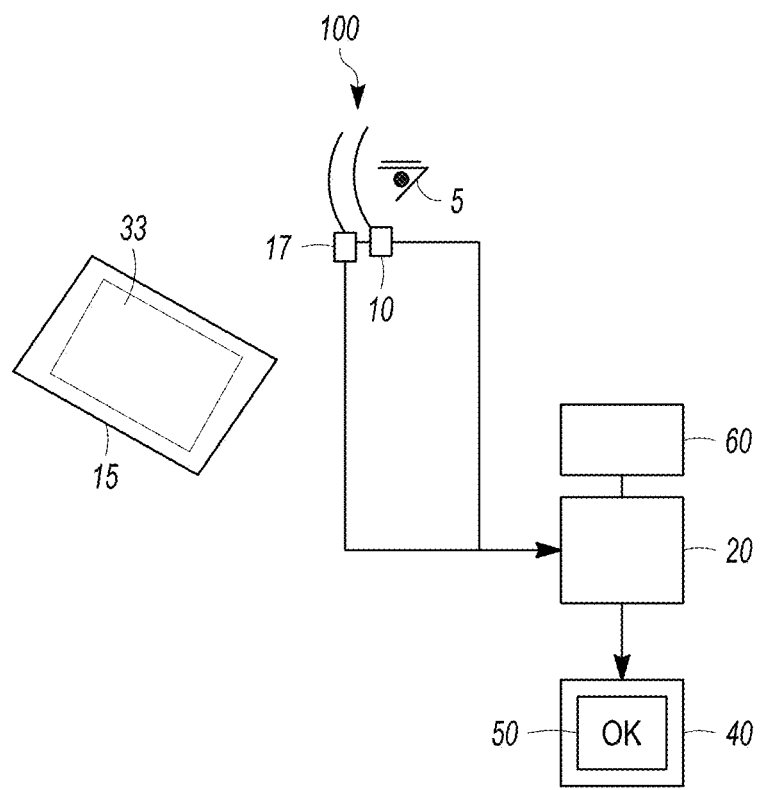

Reference is now made to FIG. 1, showing a system for detecting a neurological disorder or neurological function of a subject [5], according to some embodiments of the invention.

System comprises an eye tracker [10], a means for measuring a pupil diameter [17], a processor [20], and a display means [40].

Eye tracker can be of any type known in the art; for example, an eye-attached tracker, an optical eye tracker, or an electrooculographic eye tracker.

Means for measuring pupil diameter may comprise, for example, a camera configured to acquire an image of the eye and a processing unit for measuring the pupil diameter from the image. Alternatively to a processing unit, means for measuring a pupil diameter can comprise a display of the image with manual measurement made while viewing the display.

Eye tracker and means for measuring a pupil diameter are in communicative connection with processor [20]. The communicative connections can be of any form(s) known in the art, and can be either wired (e.g., USB, parallel port, or similar) or wireless (e.g. WiFi, Bluetooth, or similar).

Processor receives and executes instructions stored in one or more memory media [60], such as RAM, CD/DVD, HDD, flash memory, and/or any suitable medium. The instructions command processor to: 1) receive eye-tracking data from eye tracker [10]; 2) receive pupil diameter data from means of measuring pupil diameter; 3) analyze the eye-tracking and pupil diameter data (further explained herein); 4) report in a test report 50, for display on display means [40], of a detection or non-detection of one or more disorders of memory binding function in subject [5]. Display means can be a monitor, a screen of a mobile device such as a smartphone, a printout, or any suitable means of displaying test report [50]. Processor may store in memory medium any of the received eye-tracking data, intermediate results at any stage(s) of the analysis, and/or test report [50].

Neurological disorders detected by system can include reading function, such as a compromise in encoding and recognition of targets, a compromise in attentional processes, a compromise in cognitive resources, or any combination thereof. In other embodiments the disorders detected can include Multiple sclerosis (MS), Attention deficit-hyperactive disorder (ADHD), Parkinson disorder (PD), Alzheimer disease (AD), etc.

In some embodiments, processor receives eye-tracking data from eye-tracker while subject [5] views each of one or more targets [30]. Processor measures gaze durations of subject [5] on each target viewed by subject [5]. Processor calculates an average gaze duration on each of the targets by subject [5]. If an average of the gaze durations on targets of subject [5] is longer than an average gaze duration for a control group, then processor reports in test report that a compromise in a target encoding and recognition process is detected in subject [5].

In some embodiments processor additionally, or alternatively, counts a number of ocular fixations performed by subject [5] while viewing each of the targets [30]. If the number of ocular fixations performed by subject [5] while viewing the targets is higher than for a control group, then processor reports in test report that a compromise in the attentional processes is detected in subject [5].

In some embodiments, processor receives pupil diameter data from means of measuring pupil diameter while subject [5] performs activities requiring lower cognitive effort. Processor further receives pupil diameter data from means of measuring pupil diameter while subject [5] performs activities requiring a stronger cognitive effort than for the activities requiring lower cognitive effort. If an average pupil diameter of subject 5 while performing the activities requiring the stronger cognitive effort does not show an increase over an average pupil diameter of subject [5] while performing the activities requiring lower cognitive effort, then processor reports in test report that a compromise in cognitive resources is detected in subject [5].

The control group may comprise a statistically representative cross-section in the same demographic sector as subject [5] (e.g., the same gender, race, national culture, age group, and/or other demographic features of subject [5]). Eye-tracking data for the control group may be obtained by system or otherwise gathered from previous research studies and/or clinical studies. Where the average gaze duration or number of ocular fixations of subject [5] is within a selected margin—about one standard deviation of a distribution of the corresponding figure for the control group—of the average figure for the control group, system may treat the average gaze duration or number of ocular fixations of subject [5] as equal to the average corresponding figure for the control group.

It is understood that eye tracking data received by processor may be a series of eyeball positions measured by eye tracker [10], which processor analyzes to find gaze durations and ocular fixations of subject [5]. Alternatively, processor may receive a series of pre-processed signals from eye tracker [10], each signaling a gaze duration or that an ocular fixation has occurred. The signals may optionally be accompanied with metadata (e.g., eyeball position, time, and/or length of the ocular fixation).

Multiple Sclerosis

Figure 3A:
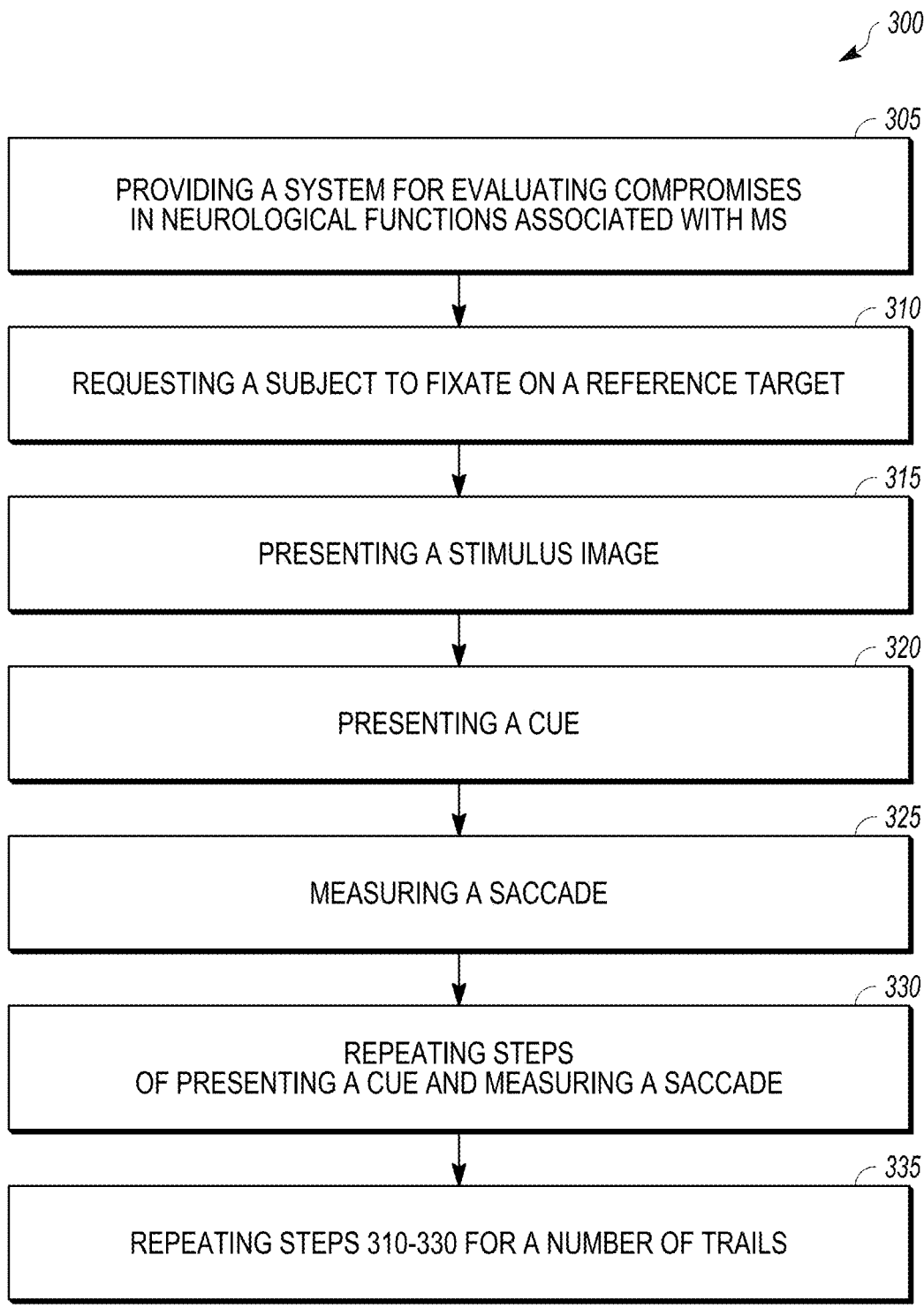
FIGS. 3A and 3B show a method for evaluating compromises in neurological functions associated with MS, according to some embodiments of the invention.
Figure 3B:
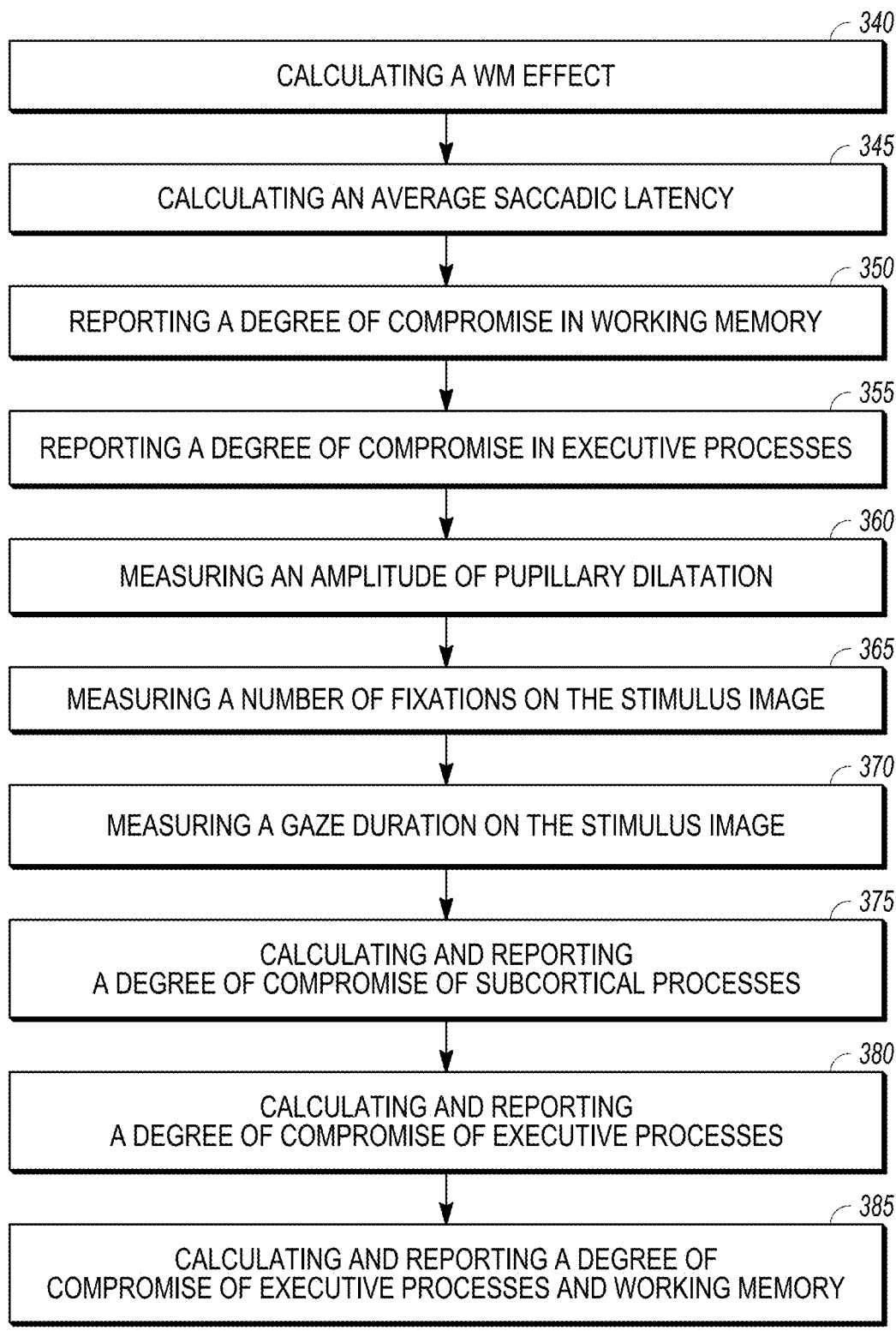

Reference is now made to FIGS. 3A and 3B, showing a method for evaluating compromises in neurological functions associated with Multiple Sclerosis [MS], according to some embodiments of the invention. Method comprises steps of:

a. providing a system for evaluating compromises in neurological functions associated with MS [305];
b. requesting a subject to fixate on a reference target of a chart [310];
c. for a number of repetitions, presenting a stimulus image in one of a plurality of zones on the chart to the subject [315]; the subject is requested to remember which zone each stimulus image appeared and in what order;
d. presenting to the subject a cue corresponding to one of the presented stimulus images [320];
e. measuring a saccade of the subject in response to the step of presenting a cue; the subject is requested to look at the zone in which was the presented stimulus image corresponding to the cue;
f. repeating steps of presenting a cue and measuring a saccade [330];
g. repeating steps b-f for a number of trials [335];
h. calculating one or more of:
  i. a WM effect (i.e. WM effect is a measure that increases when WM demand increases. For each cue number, the WM effect is represented by the ratio between the number of errors reported by the subject through all the trials, and the number of trials); and
  ii. an average saccadic latency [345], saccadic latency defined as an amount of time for the subject to initiate a saccade to the zone; and
i. reporting one or more of:
  i. a degree of compromise in working memory [350], with increased WM effect; and
  ii. a degree of compromise in executive processes [355], with increased saccadic latency;
  wherein the method further comprises additional steps, performed during the step of presenting a stimulus image [315]; during which the subject is further requested to look at the stimulus image;
j. the additional steps comprising measuring one or more of:
  i. an amplitude of pupillary dilatation of the subject [360];
  ii. a number of fixations made by the subject on the stimulus image [365]; and
  iii. a gaze duration by the subject on the stimulus image [370].

k. the additional steps further comprising calculating and reporting one or more of:
   i. a degree of compromise of subcortical processes, with an unchanged amplitude on pupil dilatation [375];
   ii. a degree of compromise of executive processes, with increased number of fixations [380]; and
   iii. a degree of compromise of executive processes and working memory, with increased gaze duration [385].

The method employs an intelligent algorithm to analyze the subject, utilizing the following variables:
   a. Total number of ocular fixations of a subject while performing the n-Back Task.
   b. Identification Number of n-Back Task Trial (i.e. if there are 20 n-Back Tasks Trials, the 5th trial is identified with the number 5. The 20th trial is identified with the number 20 etc.)
   c. Trial Part i.e., 1, 2 and 3.
   d. Part of the Trial i.e., encoding; retrieval.
   e. Pupil diameter of the subject while performing n-Back Task.
   f. Number of blinks coming from the left eye, the right eye or from both eyes.
   g. Microsaccades; Factors of Form (FF):
      i. HEWI: shows the microsacade's height/width relationship.
      ii. AREA: shows the area of the rectangle in which the microsaccade is inscribed.
      iii. LONG: is the longitude of the horizontal-vertical plane trajectory of the microsaccade.
      iv. ANG: is the sum of all the angles in the plane horizontal-vertical plane of the microsaccade.
      v. AANG: is the sum of all the absolute values of angles in radians in the plane horizontal-vertical plane of the microsaccade. These last two FF give an estimation of the microsaccadic trajectory regularity.
      vi. MOD and THETA: are the modulus and the angle of the polar coordinates of the sum of the cartesian coordinates. They give a spatial orientation of the microsaccade relative to the median of the fixation.
      vii TIME: is the time duration in milliseconds of the microsaccade.
      viii. VMIN and VMAX: are the minimum and maximum velocities of the microsaccades in degrees per second.
      ix. Microsaccade rate: is the instantaneous rate in each time bin.
      x. Directional congruency: is the congruency between the microsaccade direction and the location of the stimulus.
   h. Eye position coming from the left eye, the right eye or from both eyes (i.e., abscissa and ordinate coordinate) while performing the n-Back Task.
   i. Saccade amplitude while processing the targets.
   j. Saccade latency.
   k. Fixation sequence (i.e., ocular behavior) while processing the targets. The sequence will be available from images, from matrices, etc.
   l. Distance between the fixation point of the Right Eye and the Left Eye while performing the processing targets.
   m. Filia information of the subject (i.e., age; years of education; sex; ethnic group; occupation; hours per week of physical activity).
   n. Fixation duration while processing targets.
   o. Gaze duration while processing targets.
   p. Number of fixations on each target.
   q. Number of fixations outside each target.

The measurements made while presenting the stimulus image (feature j in method [300]) provides information during encoding, which occurs while the subject identifies the location of the visual stimulus for the first time. In pilot studies made by inventors, subjects with MS were found to be impaired when encoding visual information (e.g., subjects made many fixations on the display). Measurements during encoding are in addition to the measurements taken during recognition, when presented with cues after the visual stimuli are presented as in the study of Fielding et al. (steps a-i in method [300]). Taken together, performance of the subject during both encoding and recognition can help identify additional deficiencies (namely, degrees of compromise of subcortical processes, executive processes, and/or executive processes) and provide greater insight into the condition of the subject than performance during recognition alone.

Reading

Figure 4A:
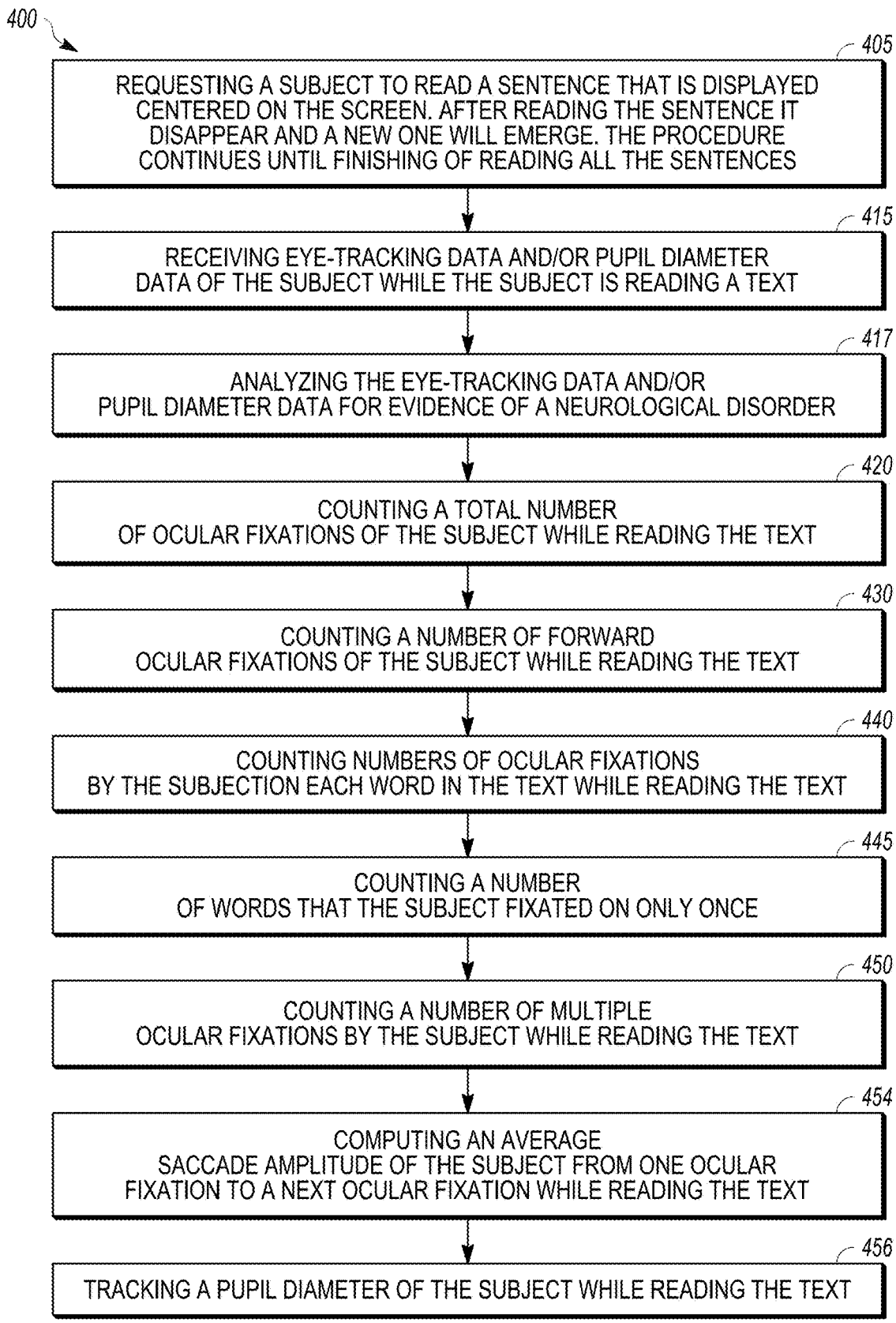
FIGS. 4A and 4B show a method for detecting one or more neurological disorders of a reading subject, according to some embodiments of the invention.
Figure 4B:
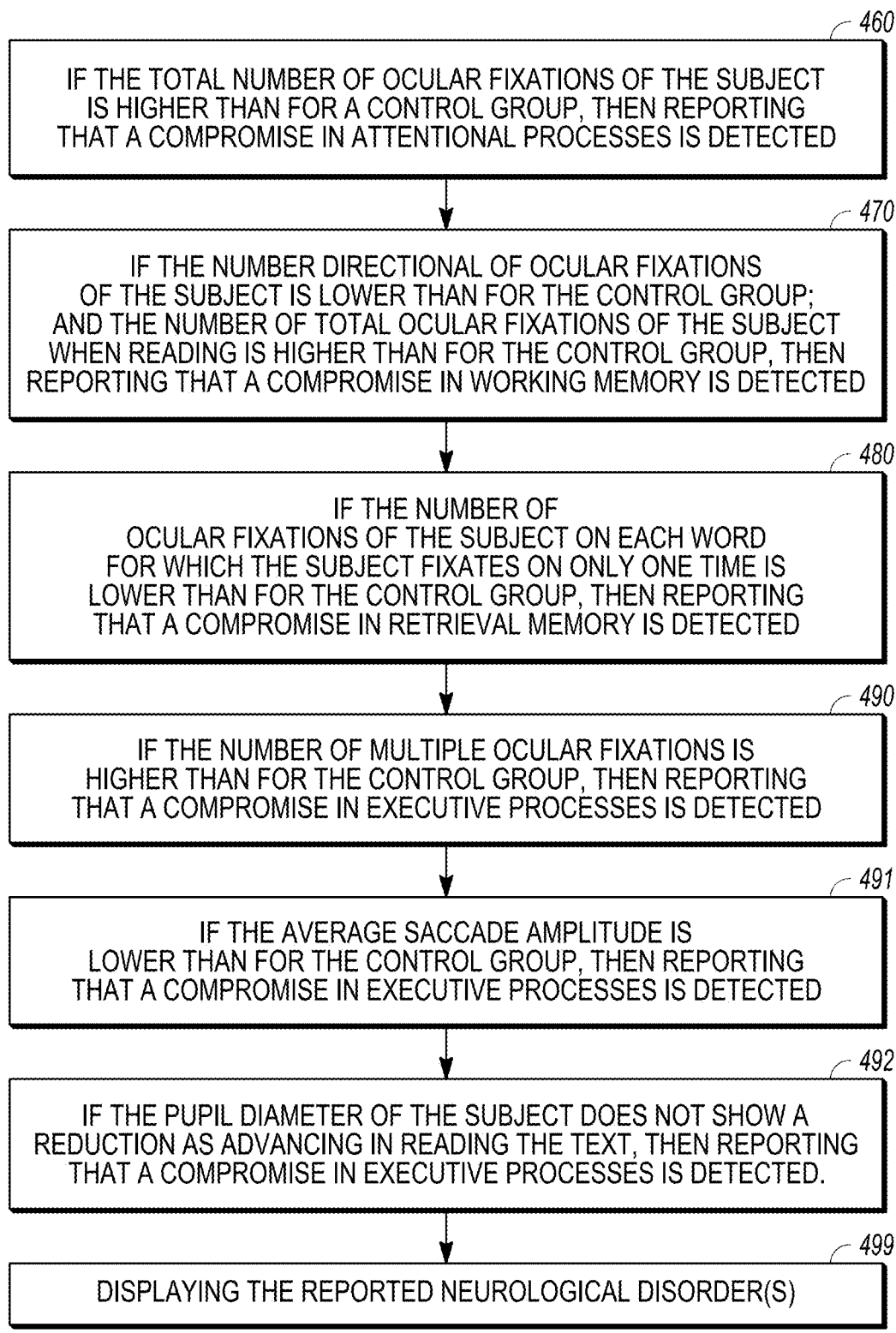

Reference is now made to FIGS. 4A and 4B, showing a method for measuring general cognitive performance and for detecting one or more neurological disorders of a subject, by measuring eye movements and/or pupil diameter of the subject while the subject is reading, according to some embodiments of the invention.

Method comprises steps of providing a system for measuring general cognitive performance and for detecting the presence of one or more neurological disorders by measuring eye movements and/or pupil diameter; receiving eye-tracking data and/or pupil diameter data of a subject reading a text; analyzing the eye-tracking data for evidence of one or more neurological disorders; and displaying a report of detection of the neurological disorder(s).

In some embodiments, method comprises steps of counting a total number of ocular fixations of the subject while the subject is reading the text [405]; and reporting that a compromise in attentional processes is detected, if the total number of ocular fixations of the subject when reading the text is higher than for a control group [460].

In some embodiments, method further comprises steps of counting a total number of ocular fixations of the subject while reading the text [405]; counting a number of forward ocular fixations of the subject while reading the text [430]; and reporting that a compromise in working memory is detected, if the number of forward ocular fixations of the subject is higher than for the control group and the number of total ocular fixations of the subject when reading is higher than for the control group [470].

Physiologically, a compromise in working memory is correlated with deterioration in the frontal lobe. In some embodiments, reporting of a compromise in working memory may be used in additional treatment. For example, if neurosurgery is indicated, method [400] may be followed by studying brain imagery of the subject's frontal lobe.

In some embodiments, method comprises steps of counting numbers of ocular fixations by the subject on each word in the text while the subject is reading the text [440]; counting a number of words that the subject fixated on only once [445]; and reporting that a compromise in retrieval memory is detected, if the number of words that subject fixated on only once is lower than for the control group [480].

Physiologically, a compromise in retrieval memory is correlated with deterioration in the temporal lobe. In some embodiments, reporting of a compromise in retrieval memory may be used in additional treatment. For example, if neurosurgery is indicated, method [400] may be followed by studying brain imagery of the subject's frontal lobe.

In some embodiments, method comprises steps of counting a number of multiple ocular fixations of subject while reading the text [450]; and reporting that a compromise in executive processes is detected, if the number of multiple ocular fixations is higher than for the control group [490].

In some embodiments, method comprises steps of computing an average saccade amplitude of the subject from one ocular fixation to a next ocular fixation while reading the text [454]; and reporting that a compromise in executive processes is detected, if the average saccade amplitude is lower than for the control group [491].

In some embodiments, method comprises steps of tracking a pupil diameter of the subject while reading the text [456]; and reporting that a compromise in executive processes is detected, if the pupil diameter of the subject does not show a reduction as advancing in reading the text [492].

Physiologically, a compromise in executive processes is correlated with deterioration in the frontal, temporal, and/or parietal lobes. In some embodiments, reporting of a compromise in executive processes [490-491-492] may be used in additional treatment. For example, if neurosurgery is indicated, method may be followed by studying brain imagery of the subject's frontal, temporal, and/or parietal lobes.

The system and method were tested on 50 Healthy Controls and 50 Mild AD Patients. Both groups read 40 regular sentences.

TABLE 1

| Test | Control Group | AD Group |
| --- | --- | --- |
| Attentional Processes | 520 (21) | 882 (317) |
| Executive Processes | 14 (8) | 37 (6) |
| Working Memory | 85 (14) | 61 (9) |
| Retrieval Memory | 30 (6) | 12 (11) |

Bibliography

The above rules are based in part upon findings in the following studies:
1. Fernández G, Mandolesi P, Rotstein N P, Colombo O, Agamennoni O, Politi L E. (2013) *Eye movement alterations during reading in patients with early Alzheimer disease.* Invest Ophthalmol Vis Sci. pii: iovs. 13-12877v1. doi: 10.1167/iovs.13-12877.
2. Fernández G., Manes F., Politi L., Orozco D., Schumacher M., Castro L., Agamennoni O., Rotstein N. (2016). *Patients with Mild Alzheimer Disease Fail When Using Their Working Memory: Evidence from the Eye Tracking Technique.* Journal of Alzheimer Disease; 50, 827-828.
3. Fernández, G., Laubrock, J., Mandolesi P., Colombo O., Agamennoni O. (2014) *Registering eye movements during reading in Alzheimer disease: difficulties in predicting upcoming words.* Journal of Clinical and Experimental Neuropsychology; 36, 302-16.
4. Fernández G., Sapognikoff M., Guinjoan S., Orozco D., Agamennoni O. (2016). *Word processing during reading sentences in patients with schizophrenia: evidences from the eyetracking technique.* COMPREHENSIVE PSYCHIATRY; 68, 193-200.
5. Fernández G, Manes F, Rotstein N, Colombo O, Mandolesi P, Politi L, Agamennoni O. (2014) *Lack of contextual-word predictability during reading in patients with mild Alzheimer disease.* Neuropsychologia; 62, 143-51.
6. Fernández G., Schumacher M., Castro L., Orozco D., Agamennoni O., (2015). *Patients with Alzheimer disease produced shorter outgoing saccades when reading sentences.* Psychiatry Research, 229, 470-478.
7. Fernández G., Biondi J., Castro S., Agamennoni O. (2017). *Pupil size behavior during online processing of sentences.* Journal of Integrative Neurosciences 15 (4) 485-496

Memory Binding

Non-limiting embodiments of the invention are now described in detail.

Figure 5:
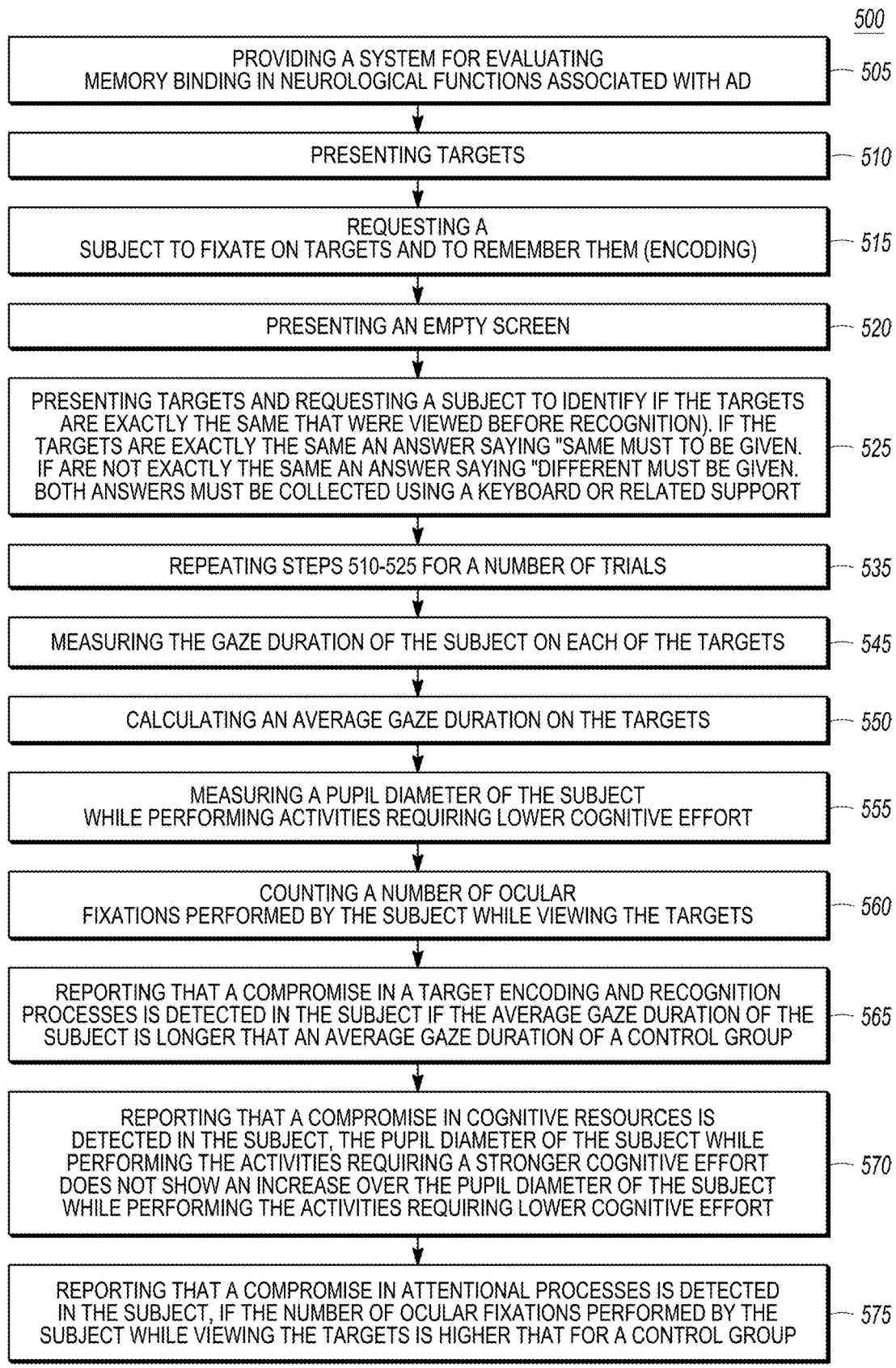
FIG. 5 shows a method for detecting a disorder of memory binding function, according to some embodiments of the invention.
Figure 5B:
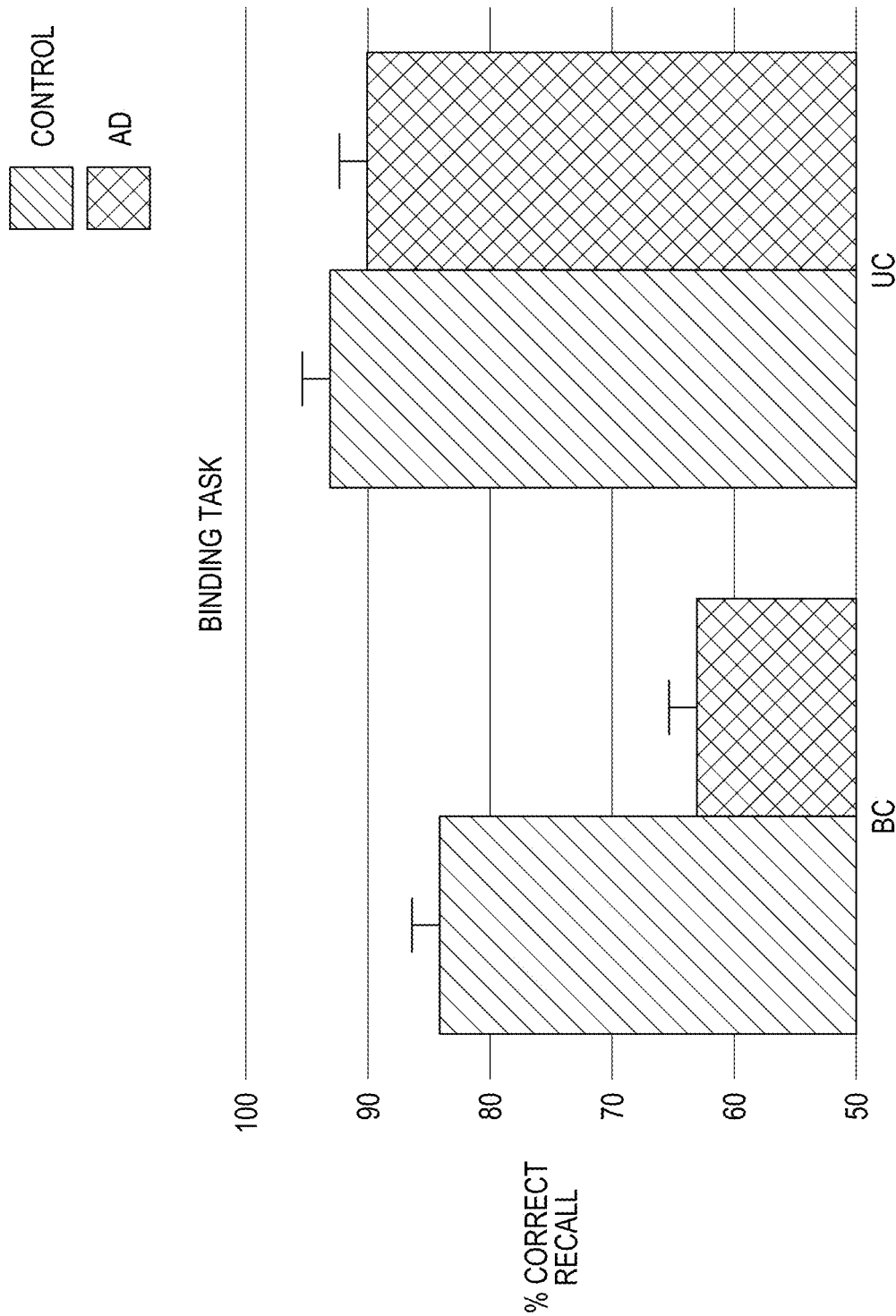
FIG. 5B shows the test results as per the evaluation method of 5A: Corrected recognition during the two experimental conditions in both controls and AD patients (error bars=standard errors of the mean).
Figure 5C:
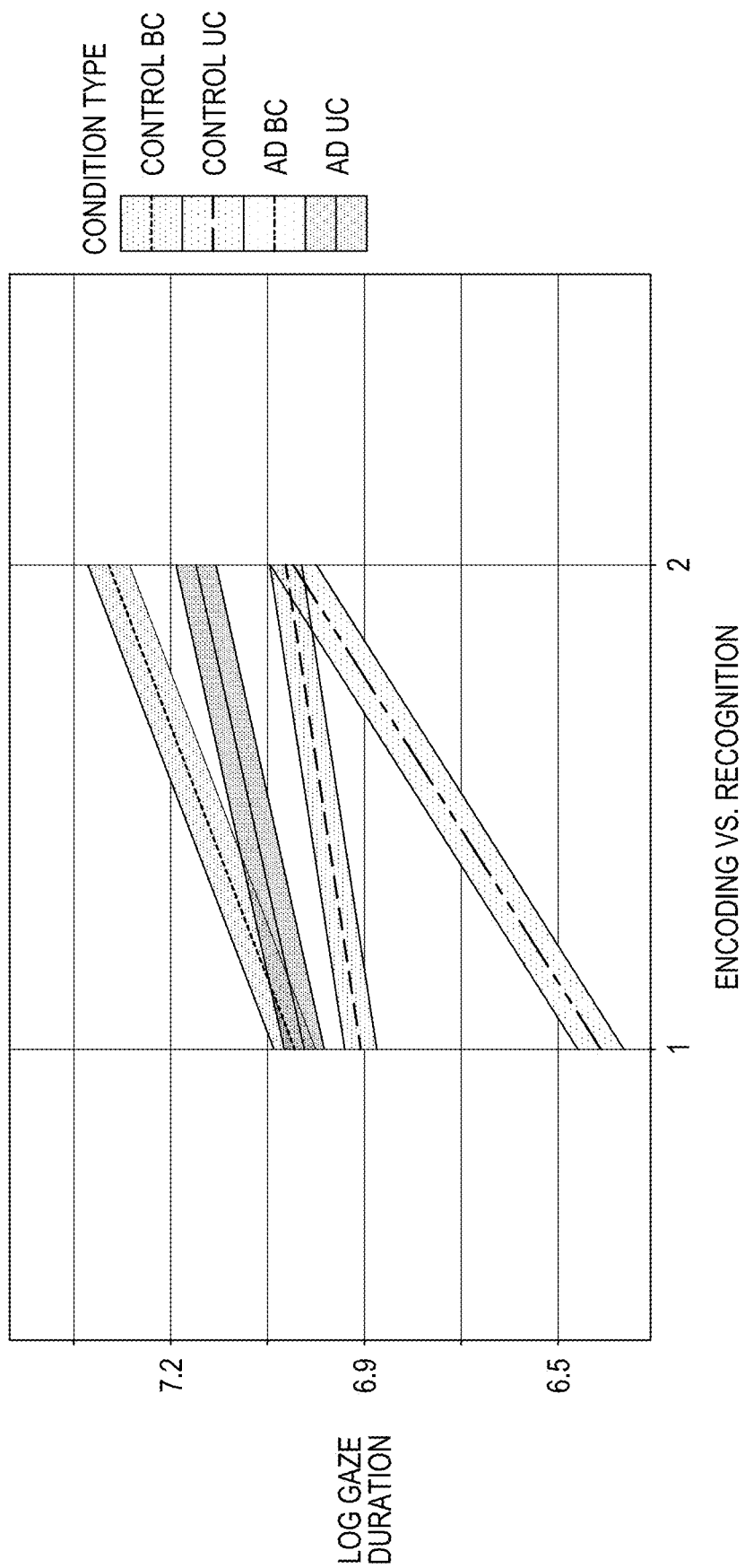
FIG. 5C shows the test results as per the evaluation method of 5A: Effect of binding task on gaze duration in control and in Alzheimer Disease (AD) patients during Encoding and Recognition moments. The panel shows the partial effects of LMM (i.e., after removal of other fixed effects and variance components). Shaded areas denote 95% confidence intervals. Gaze duration is plotted on a log scale for correspondence with the LMM.

Reference is now made to FIG. 5, showing a method for detecting a disorder of memory binding function in a subject, according to some embodiments of the invention.

Method comprises a step of providing a system for detecting a disorder of memory binding function in a subject.

In some embodiments, method comprises a step [510-535] of viewing by a subject of one or more targets; a step of measuring a gaze duration of the subject on each of said targets; a step of calculating an average gaze duration of the targets by the subject; and a step of reporting that a compromise in a target encoding and recognition process is detected in the subject, if an average of the gaze durations of the subject is longer than an average gaze duration for a control group.

In some embodiments, method comprises a step of measuring one or more pupil diameters of the subject while performing activities requiring lower cognitive effort (e.g., recognizing three targets or distinguishing between targets; and a step of reporting that a compromise in cognitive resources is detected in subject [5], if an average pupil diameter of subject [5] while performing the activities requiring a stronger cognitive effort does not show an increase over an average pupil diameter of subject [5] while performing activities requiring lower cognitive effort.

In some embodiments, method comprises a step of counting a number of ocular fixations by subject [5] while viewing the targets [30]; and a step of reporting that a compromise in attentional processes is detected in subject [5], if the number of ocular fixations performed by subject [5] while viewing the targets is higher than for the control group.

Bibliography

The above rules are based in part upon findings in the following studies:
1. Fernández G, Mandolesi P, Rotstein N P, Colombo O, Agamennoni O, Politi L E. (2013) *Eye movement alterations during reading in patients with early Alzheimer disease.* Invest Ophthalmol Vis Sci. pii: iovs. 13-12877v1. doi: 10.1167/iovs. 13-12877.
2. Fernández G., Manes F., Politi L., Orozco D., Schumacher M., Castro L., Agamennoni O., Rotstein N. (2016). *Patients with Mild Alzheimer Disease Fail When Using Their Working Memory: Evidence from the Eye Tracking Technique.* Journal of Alzheimer Disease; 50, 827-828.
3. Fernández, G., Laubrock, J., Mandolesi P., Colombo O., Agamennoni O. (2014) *Registering eye movements during reading in Alzheimer disease: difficulties in predicting upcoming words.* Journal of Clinical and Experimental Neuropsychology; 36, 302-16.
4. Fernández G., Sapognikoff M., Guinjoan S., Orozco D., Agamennoni O. (2016). *Word processing during reading sentences in patients with schizophrenia: evidences from the eyetracking technique.* COMPREHENSIVE PSYCHIATRY; 68, 193-200.

5. Fernández G, Manes F, Rotstein N, Colombo O, Mandolesi P, Politi L, Agamennoni O. (2014) *Lack of contextual-word predictability during reading in patients with mild Alzheimer disease.* Neuropsychologia; 62, 143-51.
6. Fernández G., Schumacher M., Castro L., Orozco D., Agamennoni O., (2015). *Patients with Alzheimer disease produced shorter outgoing saccades when reading sentences.* Psychiatry Research, 229, 470-478.
7. Fernández G., Biondi J., Castro S., Agamennoni O. (2017). *Pupil size behavior during online processing of sentences.* Journal of Integrative Neurosciences 15 (4) 485-496.
8. Biondi J., Fernandez G., Castro S., Agamennoni O. (2018). Eye-movement behavior identification for Alzheimer Disease diagnosis. Journal of Integrative Neurosciences (in Press).
9. Fernández, Orozco, Agamennoni, Schumacher, Sañudo, Biondi, Parra. (2018). Visual Processing during Short-Term Memory Binding in Mild Alzheimer's Disease. J Alzheimers Dis.; 63 (1): 185-194. doi: 10.3233/JAD-170728.

Parkinson Disease (PD) and Attentional Deficit Hyperactive Disorders (ADHD)

Figure 6A:
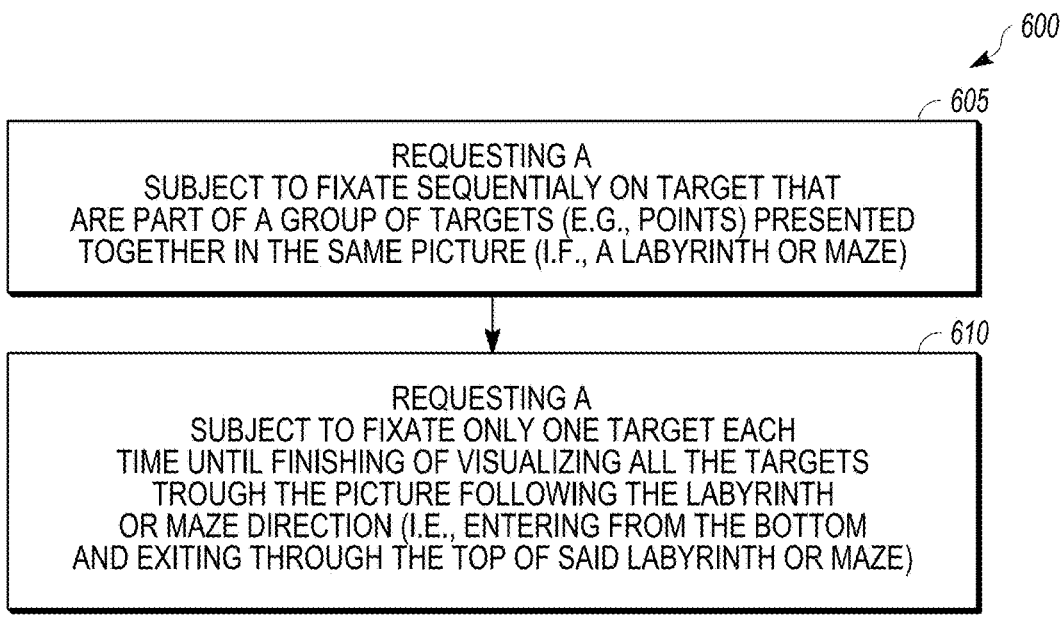
FIGS. 6A and 6B shows a method for detecting Parkinson Disorder and Attention Deficit Hyperactive Disorder
Figure 6B:
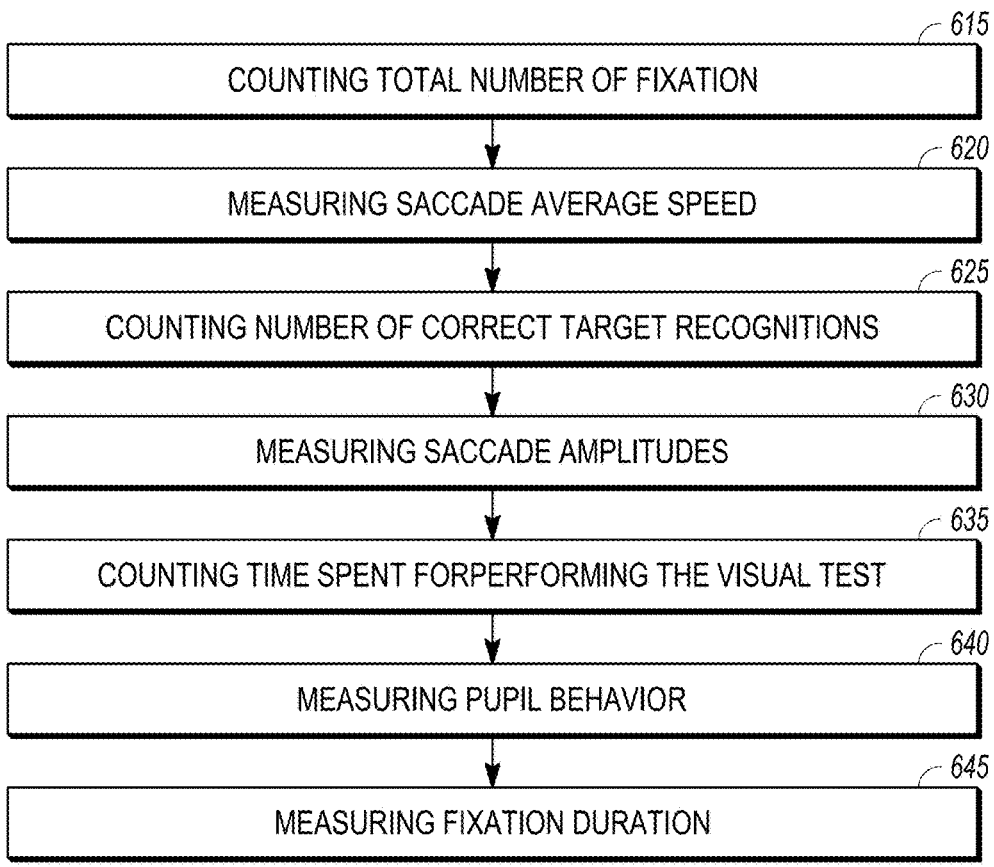

Reference is now made to FIGS. 6A and 6B showing a method for detecting one or more cognitive, neurological and behavioral impairments of a person, by measuring eye movements and/or pupil diameter of the person while the person is performing the visual test, according to some embodiments of the invention.

Method comprises steps of providing a system for detecting the presence of one or more cognitive impairments and neurological disorders by measuring eye movements while a person is visualizing, recognizing, maintaining, controlling, inhibiting and sequencing targets; receiving eye-tracking data of a person visualizing, recognizing, maintaining, controlling, inhibiting and sequencing targets; analyzing the eye-tracking data for evidence of one or more cognitive impairments and neurological disorders; and displaying a report of detection of the cognitive impairments and neurological disorder(s).

In some embodiments, method comprises steps of counting a total number of ocular fixations of the person while the person is performing the visual test; and reporting that a compromise in attentional, executive and inhibitory processes is detected, if the number of ocular fixations of the person is higher than for a control group.

In some embodiments, method comprises steps for calculating the saccade average speed of the subject [5] from one target to the other one, while the subject [5] is performing the visual test; reporting that a compromise in executive functions is detected, if the saccade average speed that person did is lower than for the control group.

Physiologically, a slower saccade speed is correlated with deterioration in frontal eye fields, basal ganglia and superior colliculus. In some embodiments, reporting of a compromise in saccade speed may be used in additional treatment.

In some embodiments, method comprises steps of counting a number of correct target recognitions of person while performing the visual test [625]; and reporting that a compromise in working memory is detected, if the number of correct target recognitions is lower than for the control group.

Physiologically, a compromise in working memory is correlated with a deterioration in Prefrontal Cortex and in the Posterior Parietal Cortex. In some embodiments, reporting of a compromise in working memory, inhibition processes and mental flexibility may be used in additional treatment.

In some embodiments, method comprises steps of computing an average saccade amplitude from one ocular fixation to a next ocular fixation [630]; and reporting that a compromise in executive processes is detected, if the average saccade amplitude is lower than for the control group.

In some embodiments, method comprises steps of tracking a pupil diameter of the person while performing the visual test [640]; and reporting that a compromise in attentional processes is detected, if the pupil diameter of the subject does not show an increase as advancing in performing the visual test.

Physiologically, a compromise in attentional processes is correlated with deterioration in the locus coeruleus, the noradrenergic system and in the superior colliculus. In some embodiments, reporting of a compromise in the executive processes may be used in additional treatment.

In some embodiments, method comprises steps of computing the total time spent by the person while performing the visual trial [635]; and reporting that a compromise in attentional processes is detected, if the total time needed for performing the trial is major that the reported for the control group.

Physiologically, a compromise in attentional and inhibitory processes and in mental flexibility is correlated with deterioration in the prefrontal cortex, the posterior parietal cortex, the prefrontal striatal cerebellar and prefrontal striatal thalamic circuits. In some embodiments, reporting of a compromise in executive processes may be used in additional treatment.

In some embodiments, method comprises steps of calculating fixation durations on targets of person while performing the visual test [645]; and reporting that a compromise in working memory is detected, if the fixation duration on targets is lower than for the control group.

Physiologically, a compromise in attentional and inhibitory processes and in mental flexibility is correlated with deterioration in the prefrontal cortex, the frontal eye fields and in the dorso-parietal cortex. In some embodiments, reporting of a compromise in executive processes may be used in additional treatment.

The method employs an intelligent algorithm to analyze the subject, utilizing the following variables:
a. Total number of ocular fixations of a subject while performing the Visual Test.
b. Identification Number of each target depending of its place in the labyrinth or maze.
c. Pupil diameter of the subject while performing the visual Test.
d. Number of blinks coming from the left eye, the right eye or from both eyes.
e. Microsaccades; Factors of Form (FF):
  i. HEWI: shows the microsacade's height/width relationship.
  ii. AREA: shows the area of the rectangle in which the microsaccade is inscribed.
  iii. LONG: is the longitude of the horizontal-vertical plane trajectory of the microsaccade.
  iv. ANG: is the sum of all the angles in the plane horizontal-vertical plane of the microsaccade.
  v. AANG: is the sum of all the absolute values of angles in radians in the plane horizontal-vertical plane of the microsaccade. These last two FF give an estimation of the microsaccadic trajectory regularity.

vi. MOD and THETA: are the modulus and the angle of the polar coordinates of the sum of the cartesian coordinates. They give a spatial orientation of the microsaccade relative to the median of the fixation.

vii TIME: is the time duration in milliseconds of the microsaccade.

viii. VMIN and VMAX: are the minimum and maximum velocities of the microsaccades in degrees per second.

ix. Microsaccade rate: is the instantaneous rate in each time bin.

x. Directional congruency: is the congruency between the microsaccade direction and the location of the stimulus.

f. Eye position coming from the left eye, the right eye or from both eyes (i.e., abscissa and ordinate coordinate) while performing the visual Task.

g. Saccade amplitude while processing the targets.

h. Saccade latency.

i. Fixation sequence (i.e., ocular behavior) while processing the targets. The sequence will be available from images, from matrices, etc.

j. Distance between the fixation point of the Right Eye and the Left Eye while performing the processing targets.

k. Filia information of the subject (i.e., age; years of education; sex; ethnic group; occupation; hours per week of physical activity).

l. Fixation duration while processing targets.

m. Number of fixations on each target.

n. Number of fixations outside each target.

o. Total visual Task time (i.e., how much time spent the subject for performing the entire trial).

This method was tested on subjects with PD and ADHD and compared to healthy controls:

TABLE 2

| Parkinson Disease | | |
|---|---|---|
| | CONTROL | PM |
| Mean GAZING (MS) | 283 (±42.4) | 359.2 (±29.5) |
| % Correct Fixation | 95% (±3) | 81% (±6) |
| ADHD | | |
| | CONTROL | ADHD |
| Mean GAZING (MS) | 283 (±42.4) | 370.3 (±33.1) |
| % Correct Fixation | 95% (±3) | 73% (±7) |

The invention claimed is:

1. A system for detecting one or more cognitive disorders that include middle temporal lobe alterations in a subject by measuring eye movements while the subject is binding visual features, said system comprising:
   a. an eye tracker;
   b. a means for measuring pupil diameters;
   c. a processor, configured to:
      i. receive eye-tracking data of a subject from said eye tracker; and
      ii. receive pupil diameter data of said subject from said means for measuring pupil diameters;
   d. a display means configured to display a test report received from said processor;
wherein said processor is further configured to analyze the eye-tracking and pupil diameter data and to report, in said test report, a detection of one or more cognitive compromises and to report, in said report, a detection of cognitive compromises in specific cognitive domains that include at leas visual working memory capabilities of said subject.

2. The system of claim 1, wherein said processor is further configured, upon receiving
   said eye-tracking data from said eye tracker, to:
   a1. calculate an average gaze duration of said subject while binding features of certain targets and when encoding, retrieving and recognizing such targets by said subject;
   b1. calculate an average gaze duration of said targets by said subject; and
   c1. report in said test report that a compromise in encoding, retrieval and recognition of targets is detected in said subject, if said average gaze duration of said subject is longer than said average gaze duration of a control group; and/or
   a2. count a number of ocular fixations performed by said subject while binding visual features of one or more targets; and
   b2. report in said test report that a compromise in attentional processes is detected in said subject, if said number of ocular fixations performed by said subject while encoding, retrieving and recognizing the targets is higher than for a control group;
   d1. receive a pupil diameter of said subject from said means for measuring pupil diameter, while said subject performs activities requiring lower and stronger cognitive effort; and
   report in said test report that a compromise in cognitive resources is detected in said subject, if said pupil diameter of said subject, while performing said
   activities requiring the stronger cognitive effort (i.e., binding features), does not show an increase over said pupil diameter of said subject while performing said activities requiring reduced/minimal cognitive effort.

3. The system of claim 1, wherein said processor is further configured, upon receiving said eye-tracking data from said eye tracker, to identify and classifying eye movement features and pupil behavior during binding features providing an output of the classifier for reporting in the test report a subject's cognitive performance and/or pathological index classification (i.e, the pathology that correspond to the subject because his/her eye movement features); and a compound value within the pathology (i.e., the level of cognitive, behavioral and biological compromise that the subject shows within a particular pathology).

4. The system of claim 1, wherein said intelligent algorithm is configured to read at least
   one input, said input selected from a group consisting of:
   a. Index of total number of ocular fixations of a subject while performing each visual Binding Task;
   b. Identification Number of Binding Trial;
   d. The Correct Behavioral Answer of the trial;
   e. Subject's Behavioral response;
   f. Part of the Trial i.e., encoding, retrieval and recognition;
   g Pupil diameter of the subject while performing the Binding task;
   h. Index of blinks coming from the left eye, the right eye or from both eyes;
   i. Microsaccades; Factors of Form (FF):
   i) HEWI: shows the micro-sacade's height/width relationship, ii) AREA: shows the area of the rectangle in which the micro-saccade is inscribed;
   iii) LONG: is the longitude of the horizontal-vertical plane trajectory of the micro-saccade;
   iv) ANG: is the sum of all the angles in the plane horizontal-vertical plane of the micro-saccade;

v) AANG: is the sum of all the absolute values of angles in radians in the plane horizontal-vertical plane of the micro-sacaccade; These last two FF give an estimation of the micro-saccadic trajectory regularity;
vi) MOD and THETA: are the modulus and the angle of the polar coordinates of the sum of the cartesian coordinates; They give an spatial orientation of the micro-saccade relative to the median of the fixation;
vii) TIME: is the time duration in milliseconds of the micro-saccade;
viii) VMIN and VMAX: are the minimum and maximum velocities of the micro-saccades in degrees per second;
ix) Micro-saccade rate: is the instantaneous rate in each time bin;
x) Directional congruency: is the congruency between the micro-saccade direction and the location of the stimulus;
j. Eye position coming from the left eye, the right eye or from both eyes (i.e., abscissa and ordinate coordinate) while performing the Binding Evaluation;
k. Saccade amplitude while processing targets;
l. Fixation sequence (i.e., ocular behavior) during processing targets; The sequence will be available from images, from matrices, etc;
m. Distance between the fixation point of the Right Eye and the Left Eye while performing the Binding Evaluation;
n. Filia information of the subject (i.e., age; years of education; sex; ethnic group; occupation; hours per week of physical activity);
o. Fixation duration while binding features of one or more targets;
p. Gaze duration while binding features of one or more targets;
q. Index of Number of fixations on each target;
r. Index Number of fixations outside each target.

5. The method of claim 1, further comprising steps of:
a. measuring gaze duration of said subject while binding features and if said average gaze duration of said subject is longer than an average gaze duration of a control group;
then reporting that a compromise in visual working memory is detected;
b. Index the total number of ocular fixations of said subject and if said number of ocular fixations performed by said subject while binding features on one or more;
targets is higher than for a control group then reporting that a compromise in the executive functions is detected;
c. measuring the pupil diameter of said subject; and
if said the pupil diameter does not increase its size while performing said activities requiring a stronger cognitive effort (i.e., binding features), then reporting that an alteration in the locus coeruleus and in the noradrenergic system is detected.

* * * * *